United States Patent
Isozumi

(10) Patent No.: US 6,576,765 B2
(45) Date of Patent: Jun. 10, 2003

(54) PROCESS FOR PREPARING AMIC ACID ESTERS

(75) Inventor: Keisuke Isozumi, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 50 days.

(21) Appl. No.: 09/980,103

(22) PCT Filed: Apr. 2, 2001

(86) PCT No.: PCT/JP01/02849

§ 371 (c)(1),
(2), (4) Date: Mar. 18, 2002

(87) PCT Pub. No.: WO01/74795

PCT Pub. Date: Oct. 11, 2001

(65) Prior Publication Data

US 2003/0032667 A1 Feb. 13, 2003

(30) Foreign Application Priority Data

Apr. 3, 2000 (JP) ........................................ 2000-100786

(51) Int. Cl.$^7$ ............................................. C07D 277/64
(52) U.S. Cl. ....................................................... 548/180
(58) Field of Search ........................ 548/180; 514/233, 514/367

(56) References Cited

U.S. PATENT DOCUMENTS 5,789,428 A * 8/1998 Shibata et al. .............. 514/367

FOREIGN PATENT DOCUMENTS

| EP | 0 775 696 A1 | 5/1997 |
| JP | 3-123765 A | 5/1991 |
| JP | 10-182616 A * | 7/1998 |

OTHER PUBLICATIONS

Y. Yukawa = M. Mukouyama, "Pine Yuki Kagaku [5th printing] [II]", Hirokawa Shoten, pp. 825–831 (1989), p. 827.

Y. Yukawa = M. Mukouyama, "Pine Yuki Kagaku [II]", Hirokawa Shoten, pp. 284–287 (1989), p. 284.

Budanvari, S. et al., (ed), "The Merck Index (Twelfth Edition)", Merck & Co., Inc., Whitehouse Station, NJ, USA, pp. 293–294 (No. 1848) (1996).

* cited by examiner

Primary Examiner—Joseph K. McKane
Assistant Examiner—Jennifer C. Murphy
(74) Attorney, Agent, or Firm—Kubovcik & Kubovcik

(57) ABSTRACT

The present invention provides a process for producing an amic acid ester represented by the following general formula (7) (wherein A is substituted or unsubstituted lower alkylene or the like; $R_1$ is substituted or unsubstituted lower alkyl or the like; and $R_3$ is hydrogen or lower alkyl), which process comprises reacting, in the presence of water, an amino acid represented by formula (1) with a halogenated carbonic acid ester represented by formula (2) (wherein X is halogen) to form an amide compound represented by formula (3), then reacting the amide compound with a halogenated carbonic acid ester represented by formula (4) (wherein $R_2$ is substituted or unsubstituted lower alkyl or the like; and X is halogen) to form, in the system, a mixed acid anhydride represented by formula (5), and reacting the mixed acid anhydride with an amine compound represented by formula (6) (wherein Het is substituted or unsubstituted heterocyclic).

9 Claims, No Drawings

PROCESS FOR PREPARING AMIC ACID ESTERS

TECHNICAL FIELD

The present invention relates to an improved process for producing an amic acid ester from an amino acid. More particularly, the present invention relates to a process for producing an amic acid ester useful as an intermediate for agrochemicals, from an amino acid (a raw material) easily industrially at a low cost.

BACKGROUND ART

A mixed acid carboxyanhydride process has been known for reaction of the acid moiety of an amic acid obtained from an amino acid (a raw material), with other amine (Nobuo Izumiya et al., "Synthesis Chemistry Series—Peptide Synthesis", pp. 126 to 129, Oct. 30, 1970, Maruzen K. K.).

In this process, first, the amino group of an amino acid is reacted with a chlorocarbonic acid ester to synthesize an amide; then, the carboxylic acid moiety of the amide is reacted with a chlorocarbonic acid ester to form a mixed acid carboxyanhydride; and the mixed acid carboxyanhydride is reacted with a corresponding amine to synthesize an intended product.

In the process, however, since the formation of the acid carboxyanhydride is slow in the presence of water, the second reaction must be conducted in a non-aqueous system using a water-free solvent. Therefore, the amide synthesized in an aqueous solvent in the first reaction needs to be dehydrated. Moreover, the second reaction needs to be conducted in a non-aqueous system as mentioned above. Accordingly, the process has a problem in that it is complicated for industrial operation.

Moreover, the dehydration step required for the synthesized amide reduces the productivity per unit time, etc. and needs a longer time for heating of the reaction system, resulting in decomposition of intended product, etc. and consequent reduction in yield. Therefore, the above conventional process has a problem in cost as well.

The present invention aims at providing a process for producing an amic acid ester useful as an intermediate for agrochemicals, from an amino acid (a raw material) easily industrially at a low cost.

DISCLOSURE OF THE INVENTION

The above aim has been achieved by the following inventions [1] to [9].

[1] A process for producing an amic acid ester represented by the following general formula (7):

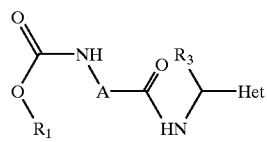

(wherein A is a substituted or unsubstituted lower alkylene group, a substituted or unsubstituted cycloalkylene group, a substituted or unsubstituted arylene group, a substituted or unsubstituted cycloalkylalkylene group or a substituted or unsubstituted aralkylene group; $R_1$ is a substituted or unsubstituted lower alkyl group, a substituted or unsubstituted cycloalkyl group, a substituted or unsubstituted aryl group, a substituted or unsubstituted cycloalkylalkyl group, a substituted or unsubstituted aralkyl group, a substituted or unsubstituted heterocyclic group or a substituted or unsubstituted heterocyclic alkyl group; and $R_3$ is a hydrogen atom or a lower alkyl group), which process comprises reacting, in the presence of water, an amino acid represented by the following general formula (1):

(wherein A has the same definition as given above) with a halogenated carbonic acid ester represented by the following general formula (2):

(wherein $R_1$ has the same definition as given above and X is a halogen atom) to form an amide compound represented by the following general formula (3):

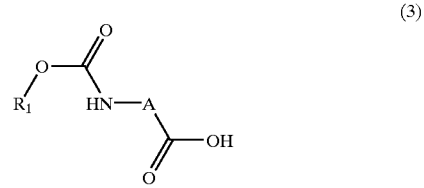

(wherein A and $R_1$ have the same definitions as given above), then reacting the amide compound with a halogenated carbonic acid ester represented by the following general formula (4):

(wherein $R_2$ is a substituted or unsubstituted lower alkyl group, a substituted or unsubstituted cycloalkyl group, a substituted or unsubstituted aryl group, a substituted or unsubstituted cycloalkylalkyl group, a substituted or unsubstituted aralkyl group, a substituted or unsubstituted heterocyclic group or a substituted or unsubstituted heterocyclic alkyl group; and X is a halogen atom) to form, in the system, a mixed acid carboxyanhydride represented by the following general formula (5):

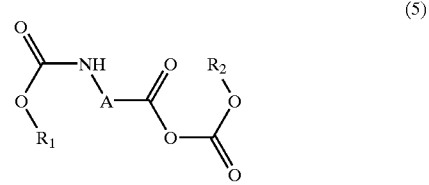

(wherein A, $R_1$ and $R_2$ have the same definitions as given above), and reacting the mixed acid carboxyanhydride with an amine compound represented by the following general formula (6) or salt thereof:

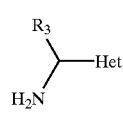
(6)

(wherein $R_3$ has the same definition as given above and Het is a substituted or unsubstituted heterocyclic group).

[2] A process for producing an amic acid ester, set forth in [1], wherein the amino acid represented by the general formula (1) is dissolved in water and reacted with the halogenated carbonic acid ester represented by the general formula (2).

[3] A process for producing an amic acid ester, set forth in [1], wherein the reaction of the amide compound represented by the general formula (3) with the halogenated carbonic acid ester represented by the general formula (4) is conducted in a reaction system comprising water or a water-organic solvent mixture.

[4] A process for producing an amic acid ester, set forth in [1], wherein the reaction of the mixed acid carboxyanhydride represented by the general formula (5) with the amine compound represented by the general formula (6) or its salt is conducted in a reaction system comprising water or a water-organic solvent mixture.

[5] A process for producing an amic acid ester, set forth in [1], wherein all the steps are conducted in one pot (one reactor).

[6] A process for producing an amic acid ester, set forth in [1], wherein the amino acid represented by the general formula (1) is valine and the chlorocarbonic acid ester represented by the general formula (2) is isopropyl chlorocarbonate.

[7] A process for producing an amic acid ester, set forth in [6], wherein all the steps are conducted in one pot (one reactor).

[8] A process for producing an amic acid ester, set forth in [1], wherein the amino acid represented by the general formula (1) is an optically active valine and the amine represented by the general formula (6) is an optically active 1-(6-fluorobenzothiazol-2-yl)ethylamine.

[9] A process for producing an amic acid ester, set forth in [8], wherein all the steps are conducted in one pot (one reactor).

The present inventors made a study in order to achieve the above aim. As a result, the present inventors surprisingly found out that an amic acid ester can be produced in one pot (one reactor) in the presence of water by adding, to an amino acid (prepared in the form of an aqueous solution of its alkali salt), a chlorocarbonic acid ester to form an amide compound, as necessary neutralizing the alkali present in excess with an acid, adding thereto an organic solvent (e.g. toluene) and a catalytic amount of a tertiary amine to convert the reaction system into a two-phase system, reacting further the amide compound with a chlorocarbonic acid ester in the presence of water to form a mixed acid anhydride in the reaction system in the presence of water, and reacting the mixed acid anhydride with an amine compound corresponding to the intended product (when the amine compound is in the form of a salt such as hydrochloride, sulfonate or the like, an alkali is also added); and moreover that when the raw materials used [for example, the amino acid represented by the above general formula (1) and the amine compound represented by the above general formula (6)] are optically active compounds, there can be synthesized an optically active amic acid ester in which the optical purities of the raw materials used are substantially retained. The above findings have led to the completion of the present invention.

BEST MODE FOR CARRYING OUT THE INVENTION

The process of the present invention is described in detail below.

First, description is made on the terms used in this specification.

The term "substituted or unsubstituted" referred to herein means that the group following the term may be unsubstituted or substituted with, for example, halogen atoms including fluorine atom, chlorine atom, bromine atom and iodine atom (hereinafter, "halogen atoms" have the same definition as above unless otherwise specified, and this applies to other substituents); $C_{1-6}$ straight or branched chain lower alkyl groups including methyl group, ethyl group, n-propyl group, isopropyl group, n-butyl group, isobutyl group, sec-butyl group, tert-butyl group, n-pentyl group and n-hexyl group; hydroxyl group; lower alkoxy groups [(lower alkyl)-o-groups] wherein the alkyl moiety is the above-mentioned lower alkyl group, including methoxy group, ethoxy group, n-propoxy group, isopropoxy group, n-butoxy group, isobutoxy group, sec-butoxy group, tert-butoxy group, n-pentyloxy group and n-hexyloxy group; lower alkoxycarbonyl groups [(lower alkoxy) —CO—groups] wherein the alkoxy moiety is the above-mentioned lower alkoxy group; carbamoyl group [$NH_2$—CO—]; and lower alkylcarbamoyl groups [(lower alkyl)—NH—CO—groups] wherein the alkyl moiety is the above-mentioned lower alkyl group.

The substituted or unsubstituted lower alkylene group refers to a $C_{1-6}$ straight or branched chain alkylene group which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned methylene group, ethylene group, n-propylene group, isopropylene group, n-butylene group, isobutylene group, sec-butylene group, tert-butylene group, n-pentylene group and n-hexylene group.

The substituted or unsubstituted cycloalkylene group refers to a $C_{3-6}$ cycloalkylene group which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned cyclopropylene group, cyclopentylene group and cyclohexylene group.

The substituted or unsubstituted arylene group refers to an arylene group (e.g. phenylene, naphthylene or anthranylene) which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned phenylene group, 1-naphthylene group, 2-naphthylene group and 1-anthranylene group.

The substituted or unsubstituted cycloalkylalkylene group refers to a $C_{1-6}$ straight or branched chain alkylene group substituted with $C_{3-6}$ cycloalkyl group, which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned cyclopropylmethylene group, cyclopropylethylene group, cyclohexylmethylene group and cyclopropylhexylene group.

The substituted or unsubstituted aralkylene group refers to an aralkylene group (e.g. benzylene group or phenylethylene group) which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned benzylene group and phenylethylene group.

The substituted or unsubstituted lower alkyl group refers to a $C_{1-6}$ straight or branched chain alkyl group which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned methyl group, ethyl group, n-propyl group, isopropyl group, n-butyl group, isobutyl group, sec-butyl group, tert-butyl group, n-pentyl group, n-hexyl group, hydroxymethyl group, hydroxyethyl group, methoxymethyl group, ethoxymethyl group, methoxycarbonylmethyl group, ethoxycarbonylmethyl group, carbamoylmethyl group, methylcarbamoylmethyl group, ethylcarbamoylmethyl group, methylcarbamoylethyl group and ethylcarbamoylethyl group.

The substituted or unsubstituted cycloalkyl group refers to a $C_{3-6}$ cycloalkyl group which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned cyclopropyl group, fluorocyclopropyl group, chlorocyclopropyl group, bromocyclopropyl group, iodocyclopropyl group, methylcyclopropyl group, ethylcyclopropyl group, hydroxycyclopropyl group, methoxycyclopropyl group, ethoxycyclopropyl group, methoxycarbonylcyclopropyl group, carbamoylcyclopropyl, methylcarbamoylcyclopropyl group, cyclobutyl group, fluorocyclobutyl group, chlorocyclobutyl group, bromocyclobutyl group, iodocyclobutyl group, methylcyclobutyl group, ethylcyclobutyl group, hydroxycyclobutyl group, methoxycyclobutyl group, ethoxycyclobutyl group, methoxycarbonylcyclobutyl group, carbamoylcyclobutyl group, methylcarbamoylcyclobutyl group, cyclobutenyl group, fluorocyclobutenyl group, chlorocyclobutenyl group, bromocyclobutenyl group, iodocyclobutenyl group, methylcyclobutenyl group, ethyl cyclobutenyl group, hydroxycyclobutenyl group, methoxycyclobutenyl group, ethoxycyclobutenyl group, methoxycarbonylcyclobutenyl group, carbamoylcyclobutenyl group, methylcarbamoylcyclobutenyl group, cyclopentyl group, fluorocyclopentyl group, chlorocyclopentyl group, bromocyclopentyl group, iodocyclopentyl group, methylcyclopentyl group, ethylcyclopentyl group, hydroxycyclopentyl group, methoxycyclopentyl group, ethoxycyclopentyl group and cyclohexyl group.

The substituted or unsubstituted aryl group refers to an aryl group such as phenyl group, toluyl group, xylyl group, cumenyl group, biphenyl group, naphthyl group, anthranyl group or the like, which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned phenyl group, o-fluorophenyl group, m-fluorophenyl group, p-fluorophenyl group, o-chlorophenyl group, m-chlorophenyl group, p-chlorophenyl group, o-bromophenyl group, m-bromophenyl group, p-bromophenyl group, o-iodophenyl group, m-iodophenyl group, p-iodophenyl group, o-toluyl group, m-toluyl group, p-toluyl group, o-xylyl group, m-xylyl group, p-xylyl group, o-cumenyl group, m-cumenyl group, p-cumenyl group, o-hydroxyphenyl, m-hydroxyphenyl, p-hydroxyphenyl, o-methoxyphenyl, m-methoxyphenyl, p-methoxyphenyl, o-carbamoylphenyl, m-carbamoylphenyl, p-carbamoylphenyl, o-methylcarbamoylphenyl, m-methylcarbamoylphenyl, methylcarbamoylphenyl, 1-naphthyl group, 2-naphthyl group and 1-anthranyl group.

The substituted or unsubstituted cycloalkylalkyl group refers to a $C_{1-6}$ straight or branched chain alkyl group substituted with $C_{3-6}$ cycloalkyl, which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned cyclopropylmethyl group, fluorocyclopropylmethyl group, chlorocyclopropylmethyl group, bromocyclopropylmethyl group, iodocyclopropylmethyl group, methylcyclopropylmethyl group, 1,1-dimethylcyclopropylmethyl group, 1,2-dimethylcyclopropylmethyl group, hydroxycyclopropylmethyl group, methoxycyclopropylmethyl group, ethoxycyclopropylmethyl group, methoxycarbonylcyclopropylmethyl group, methylcarbamoylcyclopropylmethyl group, cyclopropylethyl group, cyclohexylmethyl group and cyclopropylhexyl group.

The substituted or unsubstituted aralkyl group refers to an aralkyl group (e.g. benzyl group, 1-phenylethyl group, 2-phenylethyl group, 1-phenylpropyl group, 2-phenylpropyl group, 3-phenylpropyl group or naphthylmethyl group) which may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples, there can be mentioned benzyl group, o-fluorophenylmethyl group, m-fluorophenylmethyl group, fluorophenylmethyl group, 2,3-difluorophenylmethyl group, 2,4-difluorophenylmethyl group, 2,5-difluorophenylmethyl group, 3,4-difluorophenylmethyl group, 2,3,4-trifluorophenylmethyl group, 2,3,5-trifluorophenylmethyl group, 3,4,5-trifluorophenylmethyl group, o-chlorophenylmethyl group, m-chlorophenylmethyl group, p-chlorophenylmethyl group, 2,3-dichlorophenylmethyl group, 2,4-dichlorophenylmethyl group, 2,5-dichlorophenylmethyl group, 3,4-dichlorophenylmethyl group, 2,3,4-trichlorophenylmethyl group, 2,3,5-trichlorophenylmethyl group, 3,4,5-trichlorophenylmethyl group, o-bromophenylmethyl group, m-bromophenylmethyl group, p-bromophenylmethyl group, o-iodophenylmethyl group, iodophenylmethyl group, p-iodophenylmethyl group, phenylethyl group, phenylethyl group, o-methylphenylmethyl group, m-methylphenylmethyl group, p-methylphenylmethyl group, 2,3-dimethylphenylmethyl group, 2,4-dimethylphenylmethyl group, 2,5-dimethylphenylmethyl group, 2-ethylphenylmethyl group, 3-ethylphenylmethyl group, 4-ethylphenylmethyl group, o-(n-propyl)phenylmethyl group, m-(n-propyl) phenylmethyl group, p-(n-propyl)phenylmethyl group, o-(isopropyl) phenylmethyl group, m-(isopropyl)phenylmethyl group, p-(isopropyl) phenylmethyl group, o-hydroxyphenylmethyl group, m-hydroxyphenylmethyl group, p-hydroxyphenylmethyl group, methoxyphenylmethyl group, methoxyphenylmethyl group, p-methoxyphenylmethyl group, o-ethoxyphenylmethyl group, m-ethoxyphenylmethyl group, p-ethoxyphenylmethyl group, o-methoxycarbonylphenylmethyl group, m-methoxycarbonylphenylmethyl group, p-methoxycarbonyl-phenylmethyl group, o-carbamoylphenylmethyl group, m-carbamoylphenylmethyl group, p-carbamoylphenylmethyl group, o-methoxycarbamoylphenylmethyl group, m-methoxycarbamoyl-phenylmethyl group and p-methoxycarbamoylphenylmethyl group.

The substituted or unsubstituted heterocyclic group refers to a 5- to 10-membered single or condensed heterocyclic ring having, in the ring, at least one hetero atom selected from oxygen, nitrogen and sulfur, such as pyridyl group, pyridazyl group, pyrimidyl group, pyrazinyl group, triazinyl group, pyranyl group, dioxanyl group, thianyl group, dithianyl group, furyl group, oxolanyl group, dioxofuryl group, thienyl group, oxazolyl group, isoxazolyl group, thiazolyl group, isothiazolyl group, benzofuryl group, coumaranyl group, benzothienyl group, indolizinyl group, benzoxazolyl group, benzothiazolyl group, chromenyl group, quinolinyl group, quinazolinyl group, quinoxalinyl group or the like, which ring may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position. As specific examples of such a substituted or unsubstituted heterocyclic group, there can be mentioned pyridyl group, 2-fluoropyridyl group, 4-chloropyridyl group, 2,4-dichloropyridyl group, 4-bromopyridyl group, 4-iodopyridyl group, 2-methylpyridyl group, 4-ethylpyridyl group, 2-hydroxypyridyl group, 2-methoxypyridyl group, 2-carbamoylpyridyl group, 2-methylcarbamoylpyridyl group, pyridazyl group, pyrimidyl group, pyrazinyl group, 1,3,5triazinyl group, α-pyranyl group, β-pyranyl group, 1,4-dithianyl group, furyl group, oxolanyl group, dioxofuryl group, dioxofuryl group, thienyl group, oxazolyl group, isoxazolyl group, thiazolyl group, isothiazolyl group, benzofuryl group, coumaranyl group, benzothienyl group, indolizinyl group, benzoxazolyl group, benzothiazolyl group, 2-fluorobenzothiazolyl group, 4-fluorobenzothiazolyl group, 5-fluorobenzothiazolyl group, 6-fluorobenzothiazolyl group, 7-fluorobenzothiazolyl group, 2H-chromenyl group, 4H-chromenyl group, quinolinyl group, quinazolinyl group and quinoxalinyl group.

The substituted or unsubstituted heterocyclic alkyl group refers to a $C_{1-6}$ straight or branched chain alkyl group substituted with 5- to 10-membered heterocyclic ring having, in the ring, at least one hetero atom selected from oxygen, nitrogen and sulfur (examples of the ring are pyridyl group, pyridazyl group, pyrimidyl group, pyrazinyl group, triazinyl group, pyranyl group, dioxanyl group, thianyl group, dithianyl group, furyl group, oxolanyl group, dioxofuryl group, thienyl group, oxazolyl group, isoxazolyl group, thiazolyl group, isothiazolyl group, benzofuryl group, coumaranyl group, benzothienyl group, indolizinyl group, benzoxazolyl group, benzothiazolyl group, chromenyl group, quinolinyl group, quinazolinyl group and quinoxalinyl group), which ring may be substituted with, for example, halogen atoms, lower alkyl groups, hydroxyl group, lower alkoxy groups, lower alkoxycarbonyl groups, carbamoyl group and lower alkylcarbamoyl groups. The position of each substituent and the position of each bond may be any position As specific examples of the substituted or unsubstituted heterocyclic alkyl group, there can be mentioned 2-pyridylmethyl group, 4-pyridylmethyl group, 2-fluoropyridylmethyl group, 2,4-difluoropyridylmethyl group, 4-chloropyridylmethyl group, 2-bromopyridylmethyl group, 2-iodopyridylmethyl group, 2-methylpyridylmethyl group, 4-methylpyridylmethyl group, 2-hydroxypyridylmethyl group, 2-methoxypyridylmethyl group, 2-carbamoylpyridylmethyl group, 4-methylcarbamoylpyridylmethyl group, 3-pyridazylmethyl group, 2-pyrimidylmethyl group, 2-pyrazinyl group, 2-(1,3,5-triazinyl)methyl group, α-pyran-2-yl-methyl group, thian-2-yl-methyl group, 1,4-dithian-2-yl-methyl group, 2-furylmethyl group, dioxofuran-2-yl-methyl group, 2-thienylmethyl group, oxazol-2-yl-methyl group, isoxazol-3-yl-methyl group, thiazol-2-yl-methyl group, isothiazol-3-yl-methyl group, benzofuran-2-yl-methyl group, coumaran-2-yl-methyl group, benzothiophen-2-yl-methyl group, benzothiophen-3-yl-methyl group, benzothiophen-4-yl-methyl group, benzothiophen-5-yl-methyl group, benzothiophen-6-yl-methyl group, benzothiophen-7-yl-methyl group, indolin-1-yl-methyl group, benzoxazol-2-yl-methyl group, benzthiazol-2-yl-methyl group, 4-fluorobenzothiazol-2-yl-methyl group, 5-fluorobenzothiazol-2-yl-methyl group, 6-fluorobenzothiazol-2-yl-methyl group, 7-fluorobenzothiazol-2-yl-methyl group, benzothiazol-4-yl-methyl group, benzothiazol-5-yl-methyl group, benzothiazol-6-yl-methyl group, benzothiazol-7-yl-methyl group, 2H-chromen-2-yl-methyl group, 4H-chromen-2-yl-methyl group, quinolin-2-yl-methyl group, quinazolin-2-yl-methyl group, quinoxalin-2-yl-methyl group, 1-(2-pyridyl)ethyl group, 1-(2-fluoropyridyl)ethyl group, 1-(2,4-difluoropyridyl)ethyl group, 1-(2-chloropyridyl)ethyl group, 1-(2-bromopyridyl)ethyl group, 1-(2-iodopyridyl)ethyl group, 1-(2-methylpyridyl)ethyl group, 1-(2-ethylpyridyl)ethyl group, 1-(2,4-diethylpyridyl)ethyl group, 1-(2-hydroxypyridyl)ethyl group, 1-(3-hydroxy-pyridyl)ethyl group, 1-(2-methoxypyridyl)ethyl group, 1-(4-ethoxycarbonylphenyl)ethyl group, 1-(2-carbamoylpyridyl) ethyl group, 1-(2-methylcarbamoylpyridyl)ethyl group, 1-(3-pyridazyl)ethyl group, 1-(2-pyrimidyl)ethyl group, 1-(4-pyrimidyl)ethyl group, 1-(2-pyrazinyl)ethyl group, 1-(2-(1,3,5-triazinyl))ethyl group, 1-( α-pyran-2-yl)ethyl group, 1-(β-pyran-2-yl)ethyl group, 1-(β-pyran-3-yl)ethyl group, 1-(β-pyran-4-yl)ethyl group, 1-(dioxan-2-yl)ethyl group, 1-(thian-2-yl)ethyl group, 1-(1,4-dithian-2-yl)ethyl group, 1-(2-furyl)ethyl group, 1-(oxolan-2-yl)ethyl group, 1-(dioxofuran-2-yl)ethyl group, 1-(2-thienyl)ethyl group, 1-(oxazol-2-yl)ethyl group, i-(isoxazol-3-yl)ethyl group, 1-(thiazol-2-yl)ethyl group, 1-(isothiazol-3-yl)ethyl group, 1-(benzofuran-2-yl)ethyl group, 1-(coumaran-2-yl)ethyl group, 1-(benzothiophen-2-yl)ethyl group, 1-(indolizin-1-yl)ethyl group, 1-(benzoxazol-2-yl)ethyl group, 1-(benzothiazol-2-yl)ethyl group, 1-(4-fluorobenzothiazol-2-yl)ethyl group, 1-(5-fluorobenzothiazol-2-yl)ethyl group, 1-(6-fluorobenzothiazol-2-yl)ethyl group, 1-(7-fluorobenzothiazol-2-yl)ethyl group, 1-(benzothiazol-4-yl)

ethyl group, 1-(benzothiazol-5-yl)ethyl group, 1-(benzothiazol-6-yl)ethyl group, 1-(benzothiazol-7-yl) ethyl group, 1-(2H-chromen-2-yl)ethyl group, 1-(4H-chromen-2-yl)ethyl group, 1-(quinolin-2-yl)ethyl group, 1-(quinazolin 2-yl)ethyl group, 1-(quinoxalin-2-yl)ethyl group, 2-(2-pyridyl)ethyl group, 2-(2-fluoropyridyl)ethyl group, 2-(2,4 difluoropyridyl)ethyl group, 2-(2-chloropyridyl)ethyl group, 2-(2-bromopyridyl)ethyl group, 2-(2-iodopyridyl)ethyl group, 2-(2-methylpyridyl)ethyl group, 2-(4-ethylpyridyl)ethyl group, 2-(2-hydroxypyridyl) ethyl group, 2-(2-methoxypyridyl)ethyl group, 2-(2-ethoxycarbonylpyridyl)ethyl group, 2-(2-carbamoylpyridyl) ethyl group, 2-(2-methylcarbamoylpyridyl)ethyl group, 2-(3-pyridazyl)ethyl group, 2-(4-pyridazyl)ethyl group, 2-(4-pyrimidyl)ethyl group, 2-(2-pyrazinyl)ethyl group, 2-(2-(1,3,5-triazinyl))ethyl group, 2-( α-pyran-2-yl)ethyl group, 2-(β-pyran-2-yl)ethyl group, 2-(β-pyran-3-yl)ethyl group, 2-β-pyran-4-yl)ethyl group, 2-(thian-2-yl)ethyl group, 2-(1,4-dithian-2-yl)ethyl group, 2-(2-furyl)ethyl group, 2-(oxolan-2-yl)ethyl group, 2-(dioxolan-2-yl)ethyl group, 2-(2-thienyl)ethyl group, 2(oxazol-2-yl)ethyl group, 2-(isoxazol3-yl)ethyl group, 2-(thiazol-2-yl)ethyl group, 2-(isothiazol-3-yl)ethyl group, 2-(benzofuran-2-yl)ethyl group, 2-(coumaran-2-yl) ethyl group, 2-(benzothiophen-2-yl)ethyl group, 2-(indolizin-1-yl)ethyl group, 2-(benzoxazol-2-yl)ethyl group, 2-(benzothiazol-2-yl) ethyl group, 2-(4-fluorobenzothiazol-2-yl)ethyl group, 2-(5-fluorobenzothiazon-2-yl)ethyl group, 2-(6-fluorobenzothiazol-2-yl) ethyl group, 2-(7-fluorobenzothiazol-2-yl)ethyl group, 2-(benzothiazol-4-yl) ethyl group, 2-(benzothiazol-5-yl)ethyl group, 2-(benzothiazol-6-yl)ethyl group, 2-(benzothiazol-7-yl) ethyl group, 2-(2H-chromen-2-yl)ethyl group, 2-(4H-chromen-2-yl)ethyl group, 2-(quinolin-2-yl)ethyl group, 2-(quinazolin 2-yl)ethyl group and 2-quinoxalin-2-yl)ethyl group.

Then, description is made on the process of the present invention.

First, description is made on the reaction of the amino acid represented by the general formula (1) with the halogenated carbonic acid ester represented by the general formula (2).

In the reaction, an amino acid represented by the general formula (1) is dissolved in water in the form of its alkali metal salt and is reacted, in the presence of the water, with a halogenated carbonic acid ester represented by the general formula (2) to convert the amino group of the amino acid represented by the general formula (1) into an amide.

In the reaction, the amino acid represented by the general formula (1) used as a raw material, can be any compound represented by the general formula (1). When the compound has one or more asymmetric carbon atoms, the compound may be a single pure optical isomer, or a mixture (e.g. a racemic modification) of any proportions of individual optical isomers, or a diastereomers mixture. In the reaction, the configuration of the raw material is kept even after the completion of the reaction. As specific examples of the amino acid represented by the general formula (1), there can be mentioned glycine, alanine, β-alanine, valine, norvaline, leucine, norleucine, isoleucine, serine, threonine, methionine, phenylalanine, tyrosine, γ-aminobutyric acid, anthranilic acid and p-aminobenzoic acid. Incidentally, the amino acid represented by the general formula (1) is known, or can be produced by, for example, the process described in "JIKKEN KAGAKU KOZA (4TH EDITION) compiled by THE CHEMICAL SOCIETY OF JAPAN, Vol. 22, ORGANIC SYNTHESIS IV, ACID.AMINO ACID.PEPTIDE, PP. 193–309".

The halogenated carbonic acid ester represented by the general formula (2), used in the reaction can be any compound represented by the general formula (2). As specific examples of the halogenated carbonic acid ester represented by the general formula (2), there can be mentioned chlorocarbonic acid esters such as methyl chlorocarbonate, ethyl chlorocarbonate, n-propyl chlorocarbonate, isopropyl chlorocarbonate, n-butyl chlorocarbonate, isobutyl chlorocarbonate, n-pentyl chlorocarbonate, isopentyl chlorocarbonate, neopentyl chlorocarbonate, cyclohexyl chlorocarbonate and the like. Incidentally, the halogenated carbonic acid ester represented by the general formula (2) is known, or can be produced by, for example, the process described in "Lasurewskii; Forostjam et al., 29 (1959) 3498; engl. Ausg., etc.".

In the reaction, the use amount of the halogenated carbonic acid ester represented by the general formula (2) is 0.8 to 10 moles, preferably 1.0 to 3.0 moles per mole of the amino acid represented by the general formula (1). Water used as a reaction solvent is used in an amount of 0.01 to 10 liters, preferably 0.1 to 5 liters per mole of the amino acid represented by the general formula (1).

In the reaction, the amino acid represented by the general formula (1) is beforehand made into an aqueous solution of its alkali metal salt, using an aqueous solution of an alkali metal hydroxide such as sodium hydroxide, potassium hydroxide or the like. Specifically, this can be done by dissolving the amino acid represented by the general formula (1) in an aqueous solution of an alkali metal hydroxide. In this case, the aqueous solution of an alkali metal hydroxide is used in such an amount that the alkali becomes 1 to 10 moles, preferably 2 to 3 moles per mole of the amino acid represented by the general formula (1).

In the reaction, to the aqueous solution of the alkali metal salt of the amino acid represented by the general formula (1) is added a halogenated carbonic acid ester represented by the general formula (2). The halogenated carbonic acid ester represented by the general formula (2) is preferably added dropwise at −20 to 80° C., preferably 0 to 50° C. in order to suppress the decomposition of the halogenated carbonic acid ester.

The reaction after the dropwise addition of the halogenated carbonic acid ester represented by the general formula (2) is conducted at −20 to 80° C., preferably 0 to 50° C. for 10 hours or less, preferably 2 hours or less.

Next, description is made on the reaction of the thus-produced amide compound represented by the general formula (3) with a halogenated carbonic acid ester represented by the general formula (4), for production of a mixed acid anhydride represented by the general formula (5).

In this reaction, the amide compound represented by the general formula (3) is reacted with a halogenated carbonic acid ester represented by the general formula (4) in water or a water-organic solvent mixture, to produce a mixed acid anhydride represented by the general formula (5).

In the reaction, as the amide compound represented by the general formula (3), used as a raw material, the reaction mixture obtained in the previous reaction between the amino acid represented by the general formula (1) and the halogenated carbonic acid ester represented by the general formula (2) can be used per se in the same reactor and the reaction product obtained in the previous reaction need not be isolated.

The halogenated carbonic acid ester represented by the general formula (4), used in the reaction can be any compound represented by the general formula (4). As specific examples of the halogenated carbonic acid ester represented by the general formula (4), there can be mentioned chlorocarbonic acid esters such as methyl chlorocarbonate, ethyl chlorocarbonate, n-propyl chlorocarbonate, isopropyl chlorocarbonate, n-butyl chlorocarbonate, isobutyl chlorocarbonate, n-pentyl chlorocarbonate, isopentyl chlorocarbonate, neopentyl chlorocarbonate, cyclohexyl chlorocarbonate and the like; and bromocarbonic acid esters such as methyl bromocarbonate, ethyl bromocarbonate, n-propyl bromocarbonate, isopropyl bromocarbonate, n-butyl bromocarbonate, isobutyl bromocarbonate, n-pentyl bromocarbonate, isopentyl bromocarbonate, neopentyl bromocarbonate, cyclohexyl bromocarbonate and the like. The use amount of the halogenated carbonic acid ester represented by the general formula (4) can be 0.5 to 10 moles, preferably 0.8 to 2.0 moles per mole of the amino acid represented by the general formula (1) used as a raw material.

In carrying out the reaction, the aqueous solution of the alkali metal salt of the amide compound represented by the general formula (3) is, as necessary, neutralized with an acid such as hydrochloric acid, sulfuric acid or the like. Thereto may be added an organic solvent miscible or immiscible with water, such as aromatic hydrocarbon (e.g. toluene, xylene, ethylbenzene or chlorobenzene), ester (e.g. methyl acetate or ethyl acetate), ether (e.g. diethyl ether, tert-butyl methyl ether or dioxane), aliphatic hydrocarbon (e.g. pentane, n-hexane or cyclohexane), ketone (e.g. methyl isobutyl ketone), nitrile (e.g. acetonitrile), aprotic polar solvent (e.g. sulfolane, dimethylimidazolidinone, dimethylformamide or dimethylacet-amide). The use amount of the organic solvent when used is 0.05 to 10 liters, preferably 0.1 to 5 liters per mole of the amino acid represented by the general formula (1).

In the reaction, a halogenated carbonic acid ester represented by the general formula (4) is added to a reaction system containing the amide compound represented by the general formula (3). In this case, the halogenated carbonic acid ester represented by the general formula (4) is preferably added dropwise at −20 to 100° C., preferably −5 to 30° C. in order to suppress the decomposition of the halogenated carbonic acid ester.

The reaction after the dropwise addition of the halogenated carbonic acid ester represented by the general formula (4) is conducted at −20 to 100° C., preferably −5 to 30° C. for not more than 10 hours, preferably not more than 3 hours.

The reaction proceeds in a system free from any tertiary amine, as described previously. However, use of a tertiary amine as a catalyst is preferred for smooth proceeding of the reaction. As specific examples of the tertiary amine usable, there can be mentioned dimethylbenzylamine, triethylamine, tributylamine and pyridine. Dimethylbenzylamine is preferred. The use amount of the tertiary amine is 0.001 to 5 moles, preferably 0.05 to 2 moles per mole of the amino acid represented by the general formula (1).

Then, description is made on the production of an amic acid ester represented by the general formula (7) by reaction of the thus-produced mixed acid anhydride represented by the general formula (5) with an amine compound represented by the general formula (6).

In the reaction, the mixed acid anhydride represented by the general formula (5) is reacted with an amine compound represented by the general formula (6) in a system comprising water or a water-organic solvent mixture, whereby is produced an amic acid ester represented by the general formula (7), intended by the present invention process.

In the reaction, as the mixed acid anhydride represented by the general formula (5), used as a raw material, the reaction mixture obtained in the previous reaction between the amide compound represented by the general formula (3) and the halogenated carbonic acid ester represented by the general formula (4) can be used per se in the same reactor and the reaction product obtained in the previous reaction need not be isolated.

In the previous reaction, when an organic solvent immiscible with water is used, the aqueous layer may be removed by phase separation, in order to, for example, enable use of a reactor having a capacity as small as possible per mole of the raw material. In that case, the reaction between the compound (5) and the compound (6) proceeds in the organic solvent.

The amine compound represented by the general formula (6), used in the reaction can be any compound represented by the general formula (6). When the amine compound (6) has one or more asymmetric carbon atoms, the compound may be a single optical isomer, or a mixture of any proportions of individual optical isomers (e.g. a racemic modification), or a mixture of diastereomers. An acid addition salt thereof may also be used. As specific examples of the amine compound represented by the general formula (6) or its acid addition salt, there can be mentioned (R)-1-(6)-fluorobenzothiazol-2-yl)ethylamine, (S)-1-(6)-fluorobenzothiazol-2-yl)ethylamine, (thiophen-2-yl) methylamine, (R,S)-1-(4-methylfuran-3-yl)ethylamine, (R,S)-1-(5-methoxyisobenzofuran-6-yl)propylamine, (R,S)-1-(4-chloropyridin-2-yl)ethylamine, (R,S)-1-pyrazinylethylamine, (4,6-dimethoxypyrimidin-2-yl) methylamine, (R,S)-1-(2H-pyrrol-3-yl)ethylamine, pyrazinylmethylamine, (indol-1-yl)methylamine, (quinolizin-2-yl)methylamine, 2-methoxycarbonylbenzylamine, 4-ethoxycarbaoylbenzylamine, 4-carbamoylbenzylamine; inorganic acid salts of the above amine compounds represented by the general formula (6), such as hydrochloride, sulfate, sodium hydrogensulfate salt, phosphate, sodium dihydrogenphosphate salt, carbonate, sodium hydrogencarbonate salt and the like; and organic acid salts of the above amine compounds represented by the general formula (6), such as acetate, citrate, methanesulfonate, trifluoromethanesulfonate, benzenesulfonate, p-toluenesulfonate, p-chlorobenzenesulfonate and the like. The use amount of such a compound is 0.5 to 10 moles, preferably 0.5 to 2 moles per mole of the amino acid represented by the general formula (1).

Incidentally, for example, the above (R)-1-(6-fluorobenzothiazol-2-yl)ethylamine can be produced by adding a corresponding 2-aminothiophenol derivative alkali metal salt into an acid to reduce the pH of the salt to 6 or less and then reacting the resulting 2-aminothiophenol derivative with a corresponding amino acid-N-carboxyanhydride (see Japanese Patent Application No. 2000-100466).

When, in the reaction, the amine compound represented by the general formula (6) is used in the form of its acid addition salt, the acid addition salt is converted into a free amine compound represented by the general formula (6) by adding an alkali into the reaction system. As the alkali used therefor, there can be mentioned, for example, sodium hydroxide and potassium hydroxide. The alkali may be added into the reaction system as an aqueous solution containing 1 to 100%, preferably 10 to 50% of the alkali. The use amount of the alkali is 1 mole or more, preferably 1 mole per mole of the acid addition salt of the amine compound represented by the general formula (6).

The reaction can be conducted by adding an amine compound represented by the general formula (6) to a system containing the mixed acid anhydride represented by the general formula (5), in a system comprising water or a water-organic solvent mixture, or in a system comprising an organic solvent when, in the previous reaction, an organic solvent immiscible with water is used and, after the previous reaction, the aqueous layer is removed by phase separation, and then stirring the resulting mixture. The temperature of the reaction is −20 to 1100° C., preferably 0 to 50° C., and the period of the reaction is 10 hours or less, preferably 0.5 to 5 hours.

After the completion of the reaction, the intended product of present process, i.e. the amic acid ester represented by the general formula (7) is in dissolution in the organic phase of the reaction mixture. Therefore, the reaction mixture is subjected to phase separation by an ordinary method, the separated organic phase is, as necessary, washed with water and dried, then the organic solvent in the organic phase is distilled off to isolate the intended product. Alternatively, the reaction mixture is not subjected to phase separation and is subjected to distillation to remove the organic solvent contained in the reaction mixture and obtain an aqueous suspension of the intended product, and the suspension is filtered to isolate the intended product.

The process of the present invention is described more specifically below by way of a reference example and examples.

REFERENCE EXAMPLE 40 ml of water and 30 g (0.296 mole) of 36% hydrochloric acid were placed in a 300-ml reaction flask and cooled to 3° C. Thereto was dropwise added, at 2 to 5° C. with stirring, 48.0 g (0.056 mole) of an aqueous solution of a potassium metal salt of 2-amino-5-fluorothiophenol, followed by stirring for 1 hour. The resulting mixture had a pH of 5.23. Thereto were added 9.7 g (0.051 mole) of p-toluenesulfonic acid monohydrate and 15 ml of tetrahydrofuran, followed by stirring for 30 minutes. Then, 8.1 g (0.055 mole) of D-alanine-N-carboxyanhydride (purity: 78.3%) was added at 0° C. Aging was conducted at 15 to 20° C. for 18 hours. The resulting crystals were collected and dried at 60° C. to obtain 16.6 g of [2-(6-fluorobenzothiazolyl)]ethylamine.4-methylbenzenesulfonate (purity: 93.5%). The yield was 82.8% relative to the potassium metal salt of 2-amino-5-fluorothiophenol.

Example 1

16.1 g (0.092 mole) of 23% sodium hydroxide, 10 ml of water and 4.7 g (0.04 mole) of L-valine were placed in a 300-ml reaction flask, and stirred at room temperature for 30 minutes. Thereto was dropwise added 5.9 g (0.048 mole) of isopropyl chlorocarbonate at room temperature, followed by stirring for 1 hour. The resulting mixture was neutralized with concentrated hydrochloric acid. Thereto were added 100 ml of toluene and 0.06 g (0.0004 mole) of N,N-dimethylaminobenzylamine. Then, 4.7 g (0.038 mole) of isopropyl chlorocarbonate was added dropwise at room temperature, followed by stirring for 1 hour. Thereafter, there was added 14.0 g (0.038 mole) of (R)-1(6-fluorobenzothiazol-2-yl)]ethylamine.4-methylbenzenesulfonate (purity: 97.4%, optical purity: 99.2% ee) produced according to the above Reference Example. Further, 15.2 g (0.038 mole) of 10% sodium hydroxide was added dropwise at room temperature, followed by stirring for 2 hours. 50 ml of water was added; the resulting mixture was heated to 70° C. and subjected to phase separation; the toluene layer was washed with 50 ml of hot water and subjected to solvent removal to obtain 13.0 g (yield: 89.7%) of isopropyl [(S)-1-[(R)-1-(6-fluorobenzothiazol-2-yl)ethylcarbamoyl]2-methylpropyl]carbamate (purity: 97.2%, the proportion of formed intended substance in four diastereomers: 99.2%).

Example 2

16.1 g (0.092 mole) of 23% sodium hydroxide, 10 ml of water and 4.7 g (0.04 mole) of L-valine were placed in a 300-ml reaction flask, and stirred at room temperature for 30 minutes. Thereto was dropwise added 5.9 g.(0.048 mole) of isopropyl chlorocarbonate at room temperature, followed by stirring for 1 hour. The resulting mixture was neutralized with concentrated hydrochloric acid. Thereto were added 50 ml of toluene and 0.06 g (0.0004 mole) of N,N-dimethylaminobenzylamine. Then, 4.7 g (0.038 mole) of isopropyl chlorocarbonate was added dropwise at room temperature, followed by stirring for 1 hour. Thereafter, there was dropwise added a solution of 7.5 g (0.038 mole) of (R)-1-(6-fluorobenzothiazol-2-yl)ethylamine (purity: 98.3%, optical purity: 99.0% ee) dissolved in 50 ml of toluene, produced according to the above Reference Example, followed by stirring at room temperature for 2 hours. 50 ml of water was added; the resulting mixture was heated to 70° C. and subjected to phase separation; the toluene layer was washed with 50 ml of hot water and subjected to solvent removal to obtain 13.4 g (yield: 92.4%) of isopropyl [(S)-1-[(R)-1(6-fluorobenzothiazol-2-yl) ethylcarbamoyl]-2-methylpropyl]carbamate (purity: 96.3%, the proportion of formed intended substance in four diastereomers: 98.5%).

Industrial Applicability

The present invention provides a process for producing an amic acid ester useful as an intermediate for production of agrochemicals, easily industrially at a low cost. The present process proceeds even in the presence of water and can be carried out in one pot (one reactor) as necessary.

When the raw materials used [e.g. the amino acid represented by the general formula (1) and the amine compound represented by the general formula (6)] are optically active compounds, an optically active amic acid ester can be synthesized without giving rise to a substantial reduction in the optical purities of the raw materials and therefore with their optical purities being retained. Therefore, the present process can be used also for production of an intermediate for optically active agrochemicals. Thus, the present process has a very high industrial value.

What is claimed is:

1. A process for producing an amic acid ester represented by the following general formula (7):

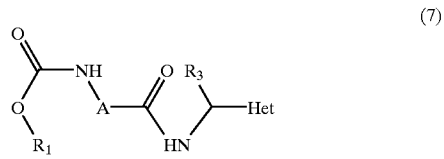

(7)

(wherein A is a substituted or unsubstituted lower alkylene group, a substituted or unsubstituted cycloalkylene group, a substituted or unsubstituted arylene group, a substituted or unsubstituted cycloalkylalkylene group or a substituted or unsubstituted aralkylene group; $R_1$ is a substituted or unsubstituted lower alkyl group, a substituted or unsubstituted cycloalkyl group, a substituted or unsubstituted aryl group, a substituted or unsubstituted cycloalkylalkyl group, a substituted or unsubstituted aralkyl group, a substituted or unsubstituted heterocyclic group or a substituted or unsubstituted heterocyclic alkyl group; and $R_3$ is a hydrogen atom or a lower alkyl group), which process comprises reacting, in the presence of water, an amino acid represented by the following general formula (1):

(1)

(wherein A has the same definition as given above) with a halogenated carbonic acid ester represented by the following general formula (2):

(2)

(wherein $R_1$ has the same definition as given above and X is a halogen atom) to form an amide compound represented by the following general formula (3):

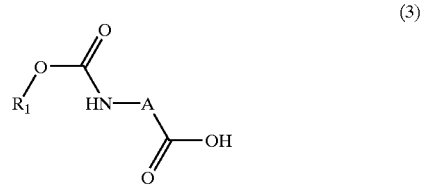

(3)

(wherein A and $R_1$ have the same definitions as given above), then reacting the amide compound with a halogenated carbonic acid ester represented by the following general formula (4):

(4)

(wherein $R_2$ is a substituted or unsubstituted lower alkyl group, a substituted or unsubstituted cycloalkyl group, a substituted or unsubstituted aryl group, a substituted or unsubstituted cycloalkylalkyl group, a substituted or unsubstituted aralkyl group, a substituted or unsubstituted heterocyclic group or a substituted or unsubstituted heterocyclic alkyl group; and X is a halogen atom) to form, in the system, a mixed acid anhydride represented by the following general formula (5):

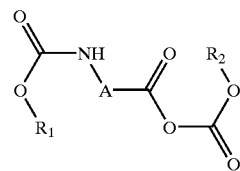

(5)

(wherein A, $R_1$ and $R_2$ have the same definitions as given above), and reacting the mixed acid anhydride with an amine compound represented by the following general formula (6):

(6)

(wherein $R_3$ has the same definition as given above and Het is a substituted or unsubstituted heterocyclic group).

2. A process for producing an amic acid ester, set forth in claim 1, wherein the amino acid represented by the general formula (1) is dissolved in water and reacted with the halogenated carbonic acid ester represented by the general formula (2).

3. A process for producing an amic acid ester, set forth in claim 1, wherein the reaction of the amide compound represented by the general formula (3) with the halogenated carbonic acid ester represented by the general formula (4) is conducted in a reaction system comprising water or a water-organic solvent mixture.

4. A process for producing an amic acid ester, set forth in claim 1, wherein the reaction of the mixed acid anhydride represented by the general formula (5) with the amine compound represented by the general formula (6) or its salt is conducted in a reaction system comprising water or a water-organic solvent mixture.

5. A process for producing an amic acid ester, set forth in claim 1, wherein all the steps are conducted in one pot (one reactor).

6. A process for producing an amic acid ester, set forth in claim 1, wherein the amino acid represented by the general formula (1) is valine and the chlorocarbonic acid ester represented by the general formula (2) is isopropyl chlorocarbonate.

7. A process for producing an amic acid ester, set forth in claim 6, wherein all the steps are conducted in one pot (one reactor).

8. A process for producing an amic acid ester, set forth in claim 1, wherein the amino acid represented by the general formula (1) is an optically active valine and the amine represented by the general formula (6) is an optically active 1-(6-fluorobenzothiazol-2-yl)ethylamine.

9. A process for producing an amic acid ester, set forth in claim 8, wherein all the steps are conducted in one pot (one reactor).

* * * * *

UNITED STATES PATENT AND TRADEMARK OFFICE
CERTIFICATE OF CORRECTION

PATENT NO. : 6,576,765 B2
DATED : June 10, 2003
INVENTOR(S) : Keisuke Isozumi

It is certified that error appears in the above-identified patent and that said Letters Patent is hereby corrected as shown below:

<u>Title page,</u>
Item [*] Notice, please correct to read "Subject to any disclaimer, the term of this patent is extended or adjusted under 35 U.S.C. 154(b) by 50 days" should be
-- Subject to any disclaimer, the term of this patent is extended or adjusted under 35 U.S.C. 154(b) by 0 days --.

Signed and Sealed this

Fourteenth Day of October, 2003

JAMES E. ROGAN
*Director of the United States Patent and Trademark Office*